United States Patent [19]

Weeks

[11] Plant 4,687

[45] Apr. 14, 1981

[54] ROSE PLANT

[76] Inventor: O. L. Weeks, 4759 Philadelphia St., Chino, Calif. 91710

[21] Appl. No.: 121,916

[22] Filed: Feb. 15, 1980

[51] Int. Cl.[3] ..... A01H 5/00

[52] U.S. Cl. ..... Plt./15

[58] Field of Search ..... Plt./15, 24

*Primary Examiner*—Robert E. Bagwill

*Attorney, Agent, or Firm*—Vincent G. Gioia

[57] ABSTRACT

A new hybrid tea rose variety of buttercup yellow coloring, substantially non-fading and useful both for its cut flowers and as a garden decoration.

1 Drawing Figure

1

The present invention relates to a new and distinct variety of rose plant of the hybrid tea rose class, which was originated by my crossing as seed parent the rose known as "Summer Sunshine" and an unpatented, unreleased and unnamed seedling of my creation as pollen parent.

Among the novel characteristics possessed by this new variety which distinguish it from its parents and all other varieties of which I am aware are its deep, rich, yellow coloring flowers borne on straight, strong stems. The vigorous plant produces blooms singly and in small clusters of three to four flowers. Flowers have significant petallage but open well and are long lasting on the plant and as a cut flower. Asexual reproduction by budding of the new variety as performed in San Bernardino County, Calif., shows that the foregoing and other distinguishing characteristics come true to form and are established and transmitted through succeeding propagations.

This new variety of hybrid tea rose differs from its seed parent in having a greater petallage and generally deeper coloring. Plants of the new variety are also more vigorous with strong, straight flower stems. In comparison to the pollen parent, the new variety has a brighter yellow coloring, is more floriferous and not as thorny.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with the Royal Horticultural Society Color Chart (RHSCC). The terminology used in color description herein refers to plate numbers in the aforementioned color chart, e.g., "16A" is plate 16A of the Royal Horticultural Society Color Chart.

Parentage: Seedling.

*Seed parent.*—"Summer Sunshine".

*Pollen parent.*—["Sunbonnet × Mister Lincoln"].

Class: Hybrid tea.

The following observations are made of specimens grown outdoors in Ontario, Calif. during the month of October.

I. FLOWER

Blooming habit: Intermittent to continuous.

A. Bud:

2

(1) *Size.*—Medium.

(2) *Form.*—Ovoid, pointed, with some foliaceous appendages on the green bud surface.

(3) *Color.*—When sepals first divide—16A to 16B. When petals begin to unfurl—color lightens to 16B to 16C.

(4) *Sepals.*—Simple, about same length as bud, color—136B to 136C.

(5) *Peduncle.*—Length—medium. Aspect—straight. Strength—erect. Color—136B.

B. Bloom:

(1) *Size.*—Average size when fully expanded—about 3½ to 4½ inches.

(2) *Borne.*—Singly and clusters of 3 to 4 blooms.

(3) *Form.*—High centered, ovoid at first becoming globular; petals are tightly rolled outward at first becoming loosely rolled at maturity.

(4) *Petalage.*—Number of petals under normal conditions—about 38 to 44.

(5) *Color.*—Petal coloring is generally 16A to 16B but as bloom opens and ages, color lightens to buttercup yellow 16C and 16D. Partially opened blooms often display different yellow shades; deeper yellow toward center and paler yellow toward perimeter. As bloom ages further (open bloom), individual petals have somewhat deeper yellow (16A to 16B) coloring toward point of attachment and outer portions of petals are lighter (16D or 12D).

C. Petals:

(1) *Texture.*—Thick.

(2) *Appearance.*—Top petal surface velvety, underside—leathery.

(3) *Form.*—Acuminate.

(4) *Arrangement.*—Regularly arranged, petals quill to star-like points.

(5) *Petaloids in center.*—Few.

(6) *Persistence.*—Drop off cleanly.

(7) *Fragrance.*—Moderate.

(8) *Lasting quality.*—Long lasting on plant and as cut flower.

2. REPRODUCTIVE ORGANS

A. Stamens, filaments and anthers:

(1) *Arrangement.*—Many stamens irregularly arranged about pistils.

(2) *Color.*—Yellow.

B. Styles: Medium length, medium caliper, bunched.

C. Stigmas: Color—yellow.

D. Hips: None observed.

3. PLANT

A. Form: Upright.
B. Growth: Moderately vigorous, free branching.
C. Foliage: Compound 3 to 5 leaflets.
(1) *Size.*—Medium.
(2) *Quantity.*—Normal.
(3) *Color.*—New foliage—begins with reddish cast and matures to: Upper side—near to 137 C, D. Under side—near to 137 C, D. Old foliage: Upper side—near to 131A. Under side—near to 136B.
(4) *Shape.*—Ovoid, mucronate.
(5) *Texture.*—Leathery, not smooth.
(6) *Edge.*—Serrated.
(7) *Serration.*—Simple.
(8) *Leaf stem.*—Color—near to 137C, D. Under side—137C.

(9) *Stipules.*—Ordinary.
D. Wood:
(1) *New wood.*—Color—near 137C.
(2) *Old wood.*—Color—near 137C.
E. Thorns:
(1) *Thorns.*—Quantity (main stalk): Ordinary. On laterals from stalk—few. Form—recurved. Length—long. Color—light brown. Position—scattered.
(2) *Prickles.*—Ordinary, short, reddish green.

I claim:

1. A new and distinct variety of rose plant of the hybrid tea class, substantially as shown and described, characterized particularly by deep yellow flowers that hold color well upon aging and are borne both singly and in small clusters of 3 to 4 blooms which are long lasting on the plant and as cut flowers.

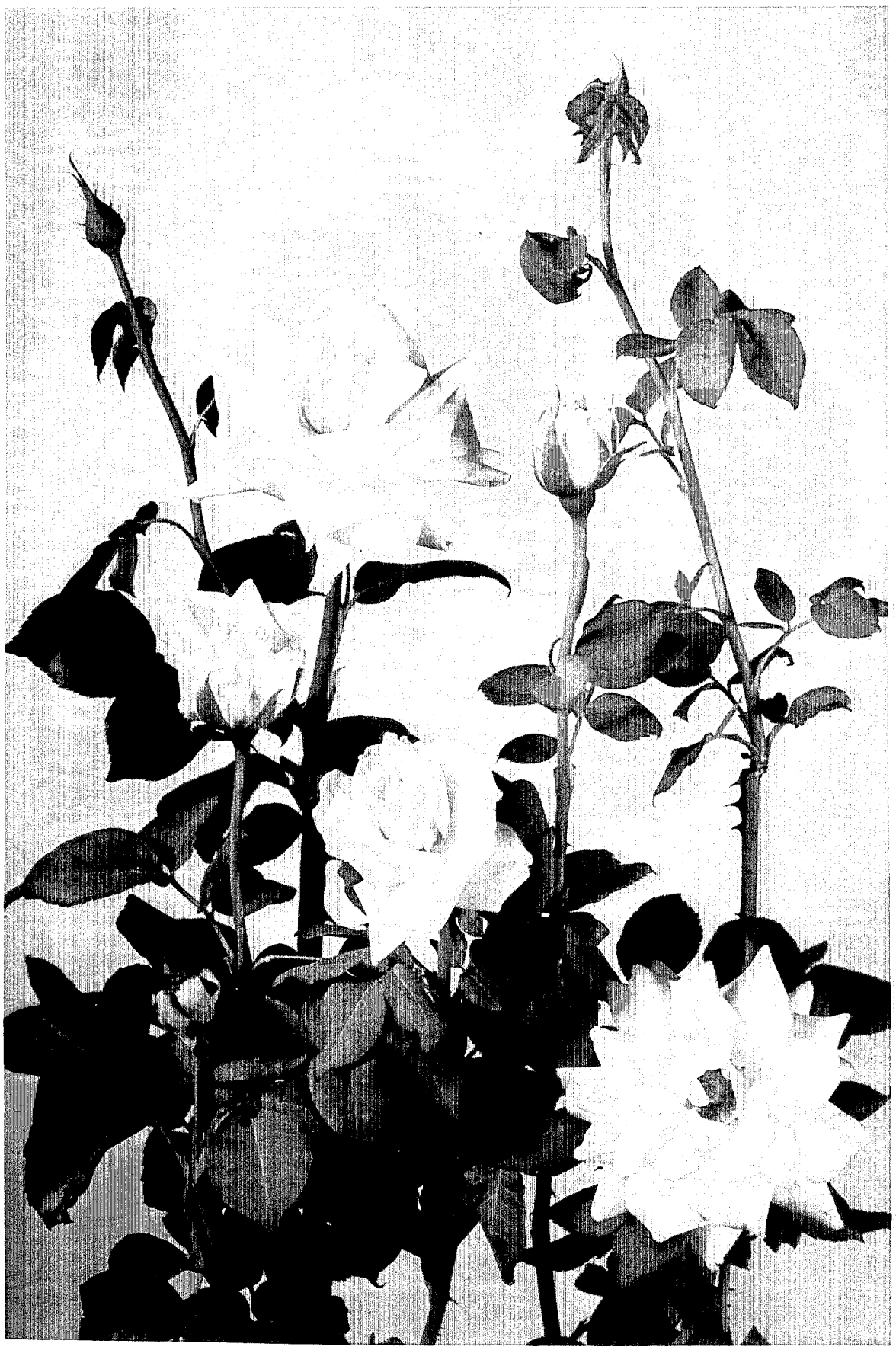

* * * * *